US008358737B2

(12) United States Patent
Tanabe (10) Patent No.: US 8,358,737 B2
(45) Date of Patent: Jan. 22, 2013

(54) APPARATUS AND METHOD FOR X-RAY TREATMENT (75) Inventor: Eiji Tanabe, Kawasaki (JP)

(73) Assignee: Accuthera Inc., Kawasaki (JP)

( * ) Notice: Subject to any disclaimer, the term of this patent is extended or adjusted under 35 U.S.C. 154(b) by 342 days.

(21) Appl. No.: 12/731,013

(22) Filed: Mar. 24, 2010

(65) Prior Publication Data
US 2010/0246767 A1 Sep. 30, 2010

(30) Foreign Application Priority Data

Mar. 25, 2009 (JP) ................................. 2009-075008

(51) Int. Cl.
*A61N 5/01* (2006.01)
*A61N 5/10* (2006.01)
*G21K 5/10* (2006.01)
*H05G 1/70* (2006.01)
*A61B 6/04* (2006.01)

(52) U.S. Cl. .................. 378/65; 378/8; 378/20; 378/69; 378/92; 378/209

(58) Field of Classification Search .................. 378/4, 8, 378/9, 15, 16, 19, 20, 64, 65, 68, 69, 91, 378/92, 95–97, 98.9, 108, 135, 137, 138, 378/193–198, 204, 205, 208–210
See application file for complete search history.

(56) References Cited

U.S. PATENT DOCUMENTS

| 6,144,875 | A | 11/2000 | Schweikard et al. |
| 6,307,914 | B1 | 10/2001 | Kunieda et al. |
| 6,993,112 | B2 * | 1/2006 | Hesse ............................. 378/65 |
| 7,289,599 | B2 * | 10/2007 | Seppi et al. ..................... 378/65 |
| 7,693,257 | B2 * | 4/2010 | Allison ........................... 378/65 |
| 7,983,380 | B2 * | 7/2011 | Guertin et al. .................... 378/4 |
| 2008/0002809 | A1 * | 1/2008 | Bodduluri ....................... 378/41 |
| 2008/0049896 | A1 * | 2/2008 | Kuduvalli ....................... 378/65 |
| 2008/0071131 | A1 | 3/2008 | Rietzel |
| 2008/0081991 | A1 | 4/2008 | West et al. |
| 2009/0154650 | A1 * | 6/2009 | Tanabe ......................... 378/137 |

FOREIGN PATENT DOCUMENTS

| JP | 3053389 | 6/2000 |
| JP | 2003-523220 | 8/2003 |
| JP | 2004-097646 A | 4/2004 |
| JP | 3748531 | 2/2006 |
| JP | 3790481 | 6/2006 |
| JP | 3881199 | 2/2007 |
| JP | 2008-68093 A | 3/2008 |
| JP | 2008-80131 A | 4/2008 |
| JP | 2008-104790 A | 5/2008 |

* cited by examiner

*Primary Examiner* — Anastasia Midkiff
(74) *Attorney, Agent, or Firm* — Orion Consulting, Ltd.; Joseph Farrar (57) ABSTRACT

An X-ray treatment apparatus comprises a low energy X-ray generator for detecting a marker, a marker sensor detecting a position of the marker fixed in the patient to a couch, and both low energy X-ray generator and the marker sensor are installed in the couch, a high energy X-ray generator for treatment, a X-ray sensor for treatment detecting the high energy X-ray for treatment. An X-ray treatment method using the X-ray treatment apparatus comprises the steps of detecting a position of a marker by the marker sensor, irradiating to a lesion the high energy X-ray for treatment, detecting the penetrated high energy X-ray for treatment by the X-ray sensor for treatment, modifying the beam profile, the dosage or/and the radiation direction of the X-ray for treatment according to the latest data of the sensors, performing the next radiation for the lesion.

17 Claims, 9 Drawing Sheets

A MOVING AMOUNT REQUIRED TO POSITION A TUMOR PORTION AT A PHYSICAL ISOCENTER IS CALCULATED FROM A LAND MARK POSITION

FIG. 4

(a) Irradiation Timing of High Energy X-ray for Treatment (b) Irradiation Timing of Low Energy X-ray for Marker Detection

APPARATUS AND METHOD FOR X-RAY TREATMENT

BACKGROUND OF THE INVENTION

1. Field of the Invention

The present invention relates to an apparatus for X-ray treatment and a treatment method using the apparatus. More particularly, the present invention relates to an apparatus and a method which can prevent the destruction of normal tissue with a new technique called MMRT (Microbeam Modulated Radiation Therapy).

2. Description of the Related Art

Disadvantageously, X-rays in an X-ray treatment are radiated to any normal tissue other than a lesion because the X-rays are radiated to the lesion through the normal tissue and the lesion moves by the breathing and other motion of the patient also. Various kinds of measures are effected for this problem.

Japanese Patent No. 3,790,481 discloses a radiation treatment apparatus which comprises a radiation generator radiating X-rays for treatment, two radiation sources irradiating X-rays for inspecting, two or more detectors, an image forming apparatus, and an analyzer. In the radiation treatment apparatus, the aperture shape of the collimator is adjusted according to calculations of the three-dimensional position and shape of the targets object part from the three-dimensional image of the inspection object part. The apparatus tracks the radiation field for treatment corresponding to the treatment object part. The apparatus cannot radiate the X-ray until the setting of the aperture shape of the collimator is completed because it tracks the moving treatment object part by changing the aperture shape of the collimator. In this apparatus, because the geometric accuracy of the radiation field depends on the setting accuracy of the aperture shape of the collimator, it is difficult to realize both rapidity and high resolution together.

Japanese Patent No. 3,881,199 discloses a radiation treatment apparatus and radiodiagnosis apparatus which can efficiently treat and diagnose with a radiation generator which can lead the breathing of the patient to be easy to take the timing and synchronization of the radiation. However, the apparatus cannot track the moving treatment object part in real time.

Japanese Patent No. 3,748,531 discloses a radiation therapy apparatus which can reduce the exposure dose to normal tissues by irradiating a tumor in the soma selectively with a large dosage. In the patent, three tumor markers embedded in the vicinity of the tumor are captured by fluoroscope from two directions. The captured two-dimensional transillumination images are digitized, and template matching is performed using the gray-level normalization cross correlation method between the digitized images and the template images of the tumor markers registered beforehand for the predetermined frame in real time to calculate the two-dimensional coordinates of the three tumor markers with a higher correlation degree on the digitized fluoroscopy images. The position of the isocenter and the three-dimensional coordinates of the three tumor markers at least are calculated based on the calculated two-dimensional coordinates of the three tumor markers, compensating for the difference from the position of isocenter in the original planning. However, it is difficult to improve the rapidity any further in this radiation therapy apparatus, because the rapidity of the continuous radiation is limited by the place recognition of the tumor markers and the settling time of the collimator. Even more particularly, in the case of radiation to the edge part of the tumor, it is difficult to avoid the normal tissues because the collimator is used, and normal tissues are damaged.

Japanese Patent No. 3,053,389 discloses a moving body tracking irradiating apparatus which is composed of a first X-ray fluoroscope, a second X-ray fluoroscope, a first and a second recognition processing section, a central arithmetic processing section, and an irradiating control section. The first X-ray fluoroscope captures the images of a tumor marker embedded in the vicinity of the tumor from a first direction, and the second X-ray fluoroscope captures the images of the tumor marker from a second direction, and the captured two-dimensional transillumination images are digitized. The first and second recognition processing sections calculate the first and the second two-dimensional coordinates of the tumor marker using the gray-level normalization cross correlation method. The central arithmetic processing section calculates the three-dimensional coordinate of the tumor marker from two-dimensional coordinates calculated by the first and second recognition processing sections. The irradiating control section controls the radiation of the treatment beam from a LINAC based on the three-dimensional coordinates of the tumor marker. Thus this apparatus can reduce the exposure dose to normal tissues by irradiating selectively to the moving tumor in the soma with a large dosage. However, it is difficult to improve the rapidity any further in this radiation therapy apparatus, because the rapidity of the continuous radiation is limited by the position recognition of the tumor markers and the settling time of the collimator. Even more particularly, in the case of radiation to the edge part of the tumor, it is difficult to avoid normal tissues because the collimator is used, and normal tissues are damaged.

Japanese Unexamined Patent Application Publication No. 2003-523220 (U.S. Pat. No. 6,144,875) discloses an apparatus and method for performing treatment on an internal target region while compensating for breathing and other motion of the patient. The apparatus comprises a first imaging device for periodically generating positional data about the internal target region and a second imaging device for continuously generating position data about one or more external markers adapted to be attached to the patient's body or any external sensor. The apparatus further comprises a processor that receives the positional data about the internal target region and the external markers in order to generate a correspondence between the position of the internal target region and the external markers and a treatment apparatus that directs the treatment towards the position of the target region of the patient based on the positional data of the external markers. However, it is difficult to improve the rapidity any further in this radiation therapy apparatus, because the rapidity of the continuous radiation is limited by the position recognition of the tumor markers and the settling time of the collimator. Even more particularly, in the case of radiation to the edge part of the tumor, it is difficult to avoid normal tissues because the collimator is used, and normal tissues are damaged.

Each previously described apparatus includes the following problems. The patient's mental and physical burdens are heavy because it is not possible to irradiate continuously and it takes time for the treatment. The accuracy of verification of the consequences of the X-ray treatment is inferior and complicated. Because the diameter of the X-ray beam cannot be thin, it is difficult to completely remove tumors without damaging normal tissue. As for the radiation direction of the apparatus, the gantry type cannot irradiate the tumor from any direction and the optimum angle.

It is an object of the present invention to provide the X-ray treatment apparatus which can track the moving tumor in real time, and can perform rapidly X-ray treatment along the shape of the object tumor with high accuracy without damage to the normal tissues by the high power and thin X-ray beam.

SUMMARY OF THE INVENTION

In a first aspect in accordance with the present invention, an X-ray treatment apparatus irradiates X-rays which intersect and penetrate a lesion from different directions to a patient who lies on a couch. The X-ray treatment apparatus includes a low energy X-ray generator and a marker sensor which detect a position of a marker fixed in the patient to the couch while keeping the predetermined position, the marker sensor is composed of an image sensor corresponding to the low energy X-ray generator, a couch operative means to make change the position and posture of the couch, an X-ray source for treatment controlling the profile and the dosage of the X-ray beam by deflecting the electron beam, an X-ray sensor for treatment detecting the X-ray which is irradiated from the X-ray source for treatment and penetrates the lesion, an X-ray source operative means to support the X-ray source and to control the position and posture of the X-ray source for treatment, a central processing unit which outputs the control signal to the X-ray source for treatment and other operative means after calculating the profile and the dosage of the X-ray source for treatment according to the position of the lesion specified by the output of the marker sensor based on the treatment plan, moreover the central processing unit modifies the treatment plan according to the output data of the X-ray sensor for treatment and outputs the next control signal to the X-ray source for treatment and other operative means. According to this X-ray treatment apparatus, because the marker is fixed in the patient while keeping the predetermined position to the lesion, the position of the lesion is specified by detecting the marker, the X-ray source for treatment can accurately irradiate to the lesion.

In a second aspect in accordance with the present invention, an X-ray treatment apparatus includes preferably an X-ray source operative means which supports an X-ray source for treatment in a head of six axis or seven axis robot arm. By this, the X-ray treatment from a wide solid angle toward the lesion is enabled.

In a third aspect in accordance with the present invention, an X-ray treatment apparatus includes preferably an X-ray source operative means which is a gantry or a toroidal rotational structure such as Calculated Tomography, supporting an X-ray source for treatment, deciding freely the direction of the radiation cooperating with the motion of the couch.

In a fourth aspect in accordance with the present invention, an X-ray treatment apparatus includes preferably an X-ray source for treatment comprising an X-ray target tube array which is composed of a plurality of the target tubes generating a thin beam of the diameter from 1 mm to 10 mm, and the accurate treatment is possible by using the X-ray treatment apparatus.

In a fifth aspect in accordance with the present invention, an X-ray treatment apparatus includes preferably an X-ray source for treatment which the activity of an X-ray target tube in the X-ray source is selected according to a treatment plan. The accurate treatment to the complicated shaped lesion is enabled by the X-ray treatment apparatus because a profile and condition of the X-ray for treatment which can be freely changed in real time by selecting the condition of the activity of each the X-ray target tube. Moreover, the X-ray treatment apparatus can improve the quality of treatment and shorten the treatment time.

In a sixth aspect in accordance with the present invention, an X-ray treatment apparatus includes preferably marker sensors which are composed of two low energy X-ray generators and image sensors corresponding to the low energy X-ray generators, and outputs the image data of the lesion and a marker which is harmless heavy metal for human body. The position of the lesion can be specified in connection with the couch by the X-ray treatment apparatus.

In a seventh aspect in accordance with the present invention, an X-ray treatment apparatus includes preferably two low energy X-ray generators and image sensors corresponding to the low energy X-ray generators, both two low energy X-ray generators and image sensors are installed in a gantry.

In an eighth aspect in accordance with the present invention, an X-ray treatment method using the X-ray treatment apparatus includes the steps of detecting a position of a marker by a marker sensor, irradiating high energy X-rays for treatment to a lesion according to a treatment plan, detecting a penetrated high energy X-ray by an X-ray sensor for treatment, modifying the treatment plan according to the result, performing the next radiation with the modified treatment plan. The data of the X-ray sensor is used for the verification after the treatment also.

In a ninth aspect in accordance with the present invention, an X-ray treatment method using the X-ray treatment apparatus includes preferably the steps of modifying a beam profile, a dosage and an radiation direction of an X-ray for treatment according to the latest data of the image data of the X-ray sensor for treatment or/and the image data of marker sensor. By this, the cyclic treatment is enabled accurately while changing the condition of the radiation, and reduces the patient's mental and physical burdens.

In a tenth aspect in accordance with the present invention, an X-ray treatment apparatus includes preferably an X-ray sensor for treatment detecting the high energy X-ray which is installed in the couch.

DESCRIPTION OF THE PREFERRED EMBODIMENTS

Figure 1A:
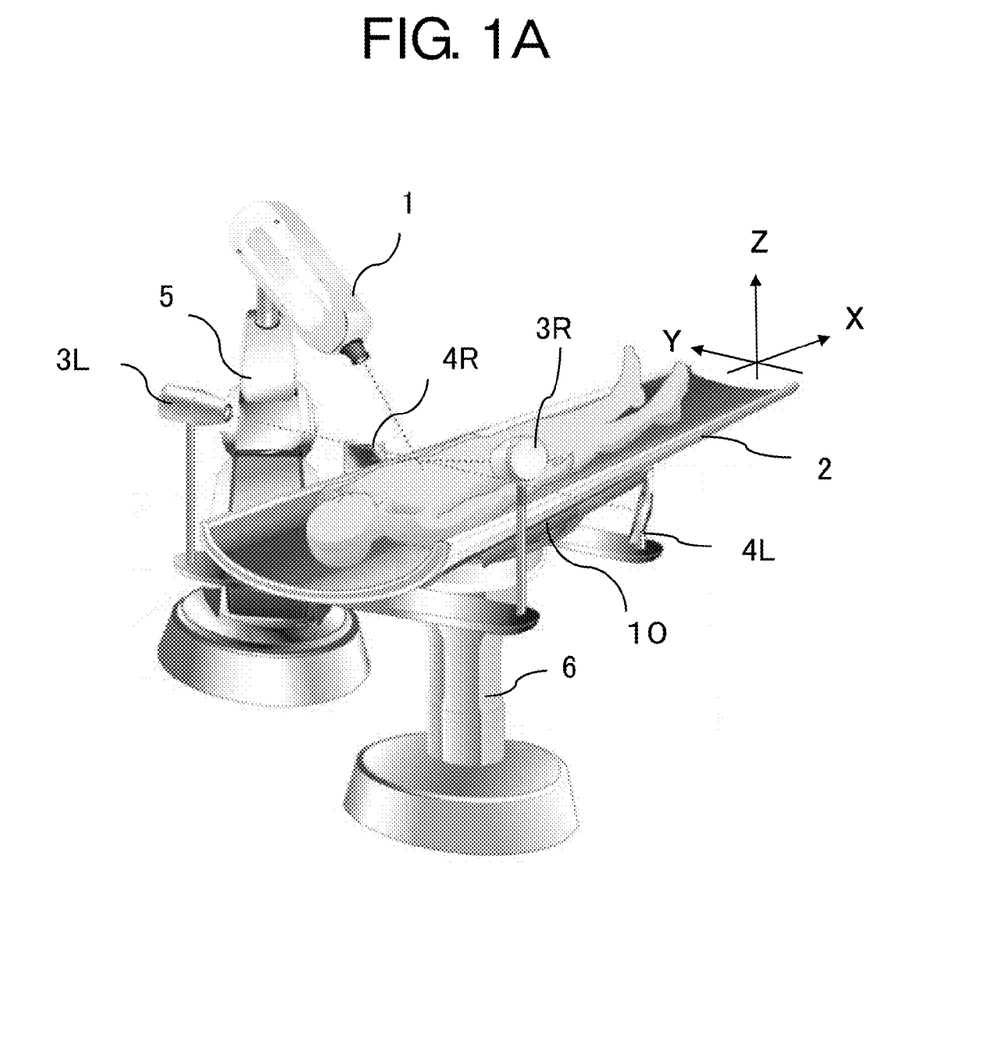
FIG. 1A shows a perspective view showing the X-ray treatment apparatus in accordance with an embodiment of the present invention.
Figure 1B:
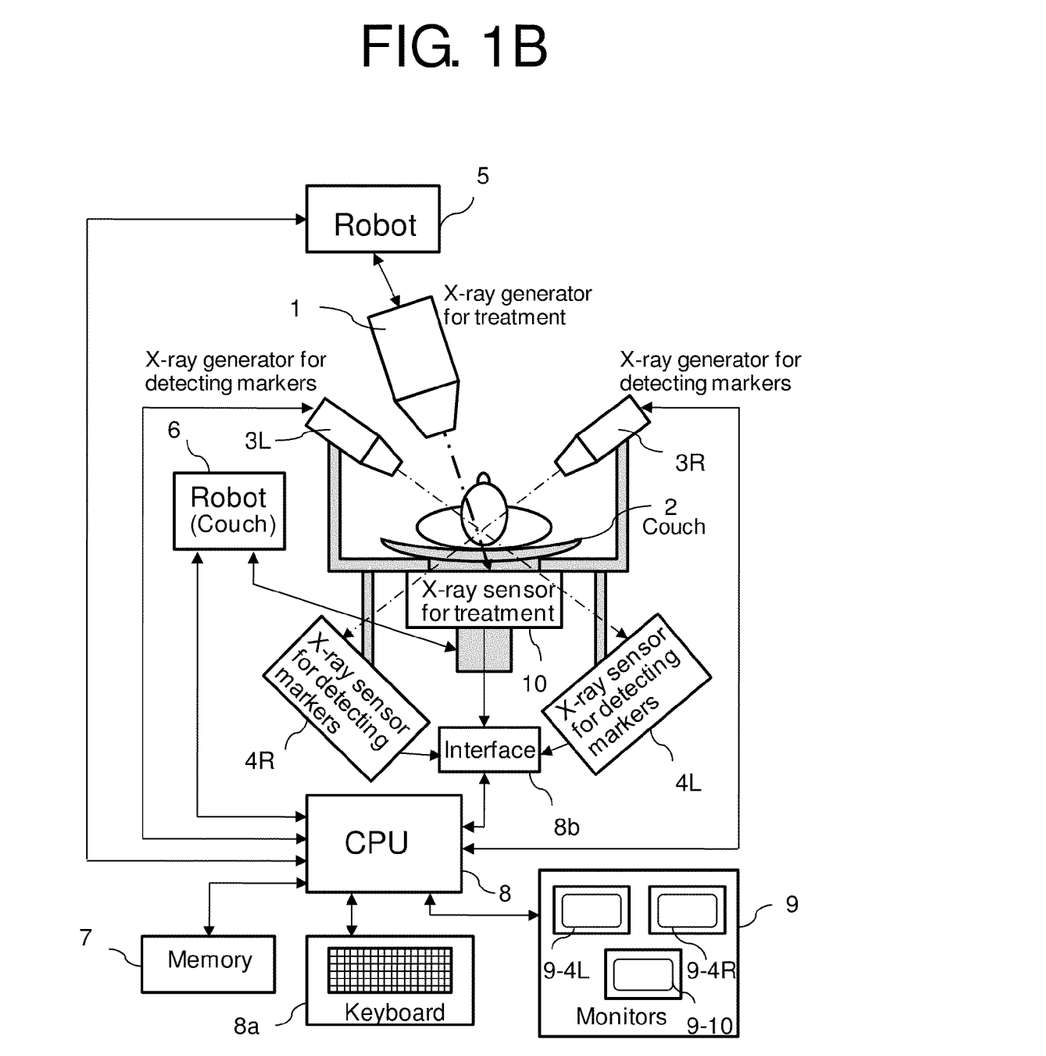
FIG. 1B shows a block diagram showing the X-ray treatment apparatus in accordance with an embodiment of the present invention.

FIG. 1A shows a perspective view showing the X-ray treatment apparatus in accordance with an embodiment of the present invention, and FIG. 1B shows a block diagram of the X-ray treatment apparatus. The following detailed description is of a case in which the lesion is a tumor.

The marker is fixed in the vicinity of a tumor in the patient while maintaining a predetermined position relative to the couch. The material of the marker is a heavy metal such as Au or Pt which is safe for the human body and absorbs X-rays well.

The marker sensor includes two low energy X-ray generators 3L, 3R, which are installed in the couch 2 and are turned to the tumor to detect the position of a marker, and two image sensors 4L, 4R corresponding to each low energy X-ray generator. The marker sensor collects the information about the tumor, which keeps the predetermined position relative to the marker and the three-dimensional position of the marker relative to the couch 2.

The position of the couch 2 is changed by the robot 6, which is the couch position attitude control means. The robot 6 supporting the couch 2 can raise or lower in the Z-axis direction in FIG. 1A, rotate to the Z-axis circumference, move in the X or Y-axis direction and rotate to the X-axis circumference.

The marker sensor specifies the three-dimensional position of the marker relative to the couch 2.

The X-ray generator 1 for treatment can control the profile and the intensity of the X-ray for treatment. The detailed configuration of the X-ray generator is described below in the first embodiment and the second embodiment of the X-ray source.

The X-ray sensor 10 for treatment installed in the couch 2 detects the X-ray for treatment which has penetrated the tumor, and obtains the profile of the X-ray.

The robot 5 supports X-ray generator 1 for treatment with the six- or seven-axis robot arm, and controls the position and direction of the X-ray generator 1 for treatment relative to the tumor.

The robot 6 is installed on the floor so that it is possible to adjust the relative position of the couch 2 to the robot 5. The robot 6 can raise or lower in the Z-axis direction in FIG. 1A, rotate to the Z-axis circumference, move to the X or Y-axis direction and rotate to the X-axis circumference.

FIG. 1B is a block diagram of an embodiment of the present invention. The X-ray generator 1 for treatment is supported by robot 5, and the X-ray sensor 10 for treatment is installed in the couch 2. The X-ray sensor 10 for treatment is composed of a flat panel and detects the state of the X-ray for treatment, such as the position, the intensity and the direction to the tumor. The X-ray sensor 10 for treatment is installed in connection with the couch 2 to detect X-rays that have penetrated the tumor. The X-ray sensor 10 for treatment can be moved with the couch 2 by the robot 6, or is installed under the couch 2 so that it can move with tracking of the movement of the X-ray generator 1. Moreover the X-ray sensor 10 can be used as a sensor to detect the state of the tumor after the X-ray treatment by decreasing the output energy level of the X-ray generator 1 for treatment.

The X-rays of the low energy X-ray generators 3L, 3R for detecting marker are detected respectively by the sensors 4L, 4R, the output signals of the sensors 4L, 4R are taken in by CPU 8 through the interface 8b, and, after image processing by the CPU 8, the images are displayed on the monitors 9-4L and 9-4R, and the data of the images are stored in the memory 7.

In this embodiment, CPU 8 calculates the suitable intensity, direction and time to treat for the tumor of which the position is specified according to the original treatment plan or the modified treatment plan by the data of the marker sensors 4L, 4R. CPU 8 instructs the operation of the robot 5 and instructs the X-ray generator 1 to operate after completing the preparation of the robot 5. The doctor can observe the situation of the treatment with the monitor unit 9.

The moving tumor can be detected by irradiating the marker, which is embedded in the vicinity of the tumor. The X-ray generators 3L, 3R for detecting the marker and the marker sensors 4L, 4R are installed in the couch 2. The energy level of the X-ray generators 3L, 3R are set in low level so as not to influence the normal tissues harmfully if more than 100,000 pulses radiations. The X-ray for detecting marker is radiated from two perpendicular directions, and penetrates the patient. The image of the embedded marker is captured by the marker sensors 4L, 4R such as flat panels installed in the couch 2. The X-ray sensor 10 for treatment is installed in the couch 2 also, and detects the intensity, radiation position and direction of the X-ray for treatment. The detected data is used to adjust the next radiation. The detected data is an important data to verify the result after the treatment also. The detected data facilitates the verification after the treatment and reduces the burden on the doctor.

Figure 4:
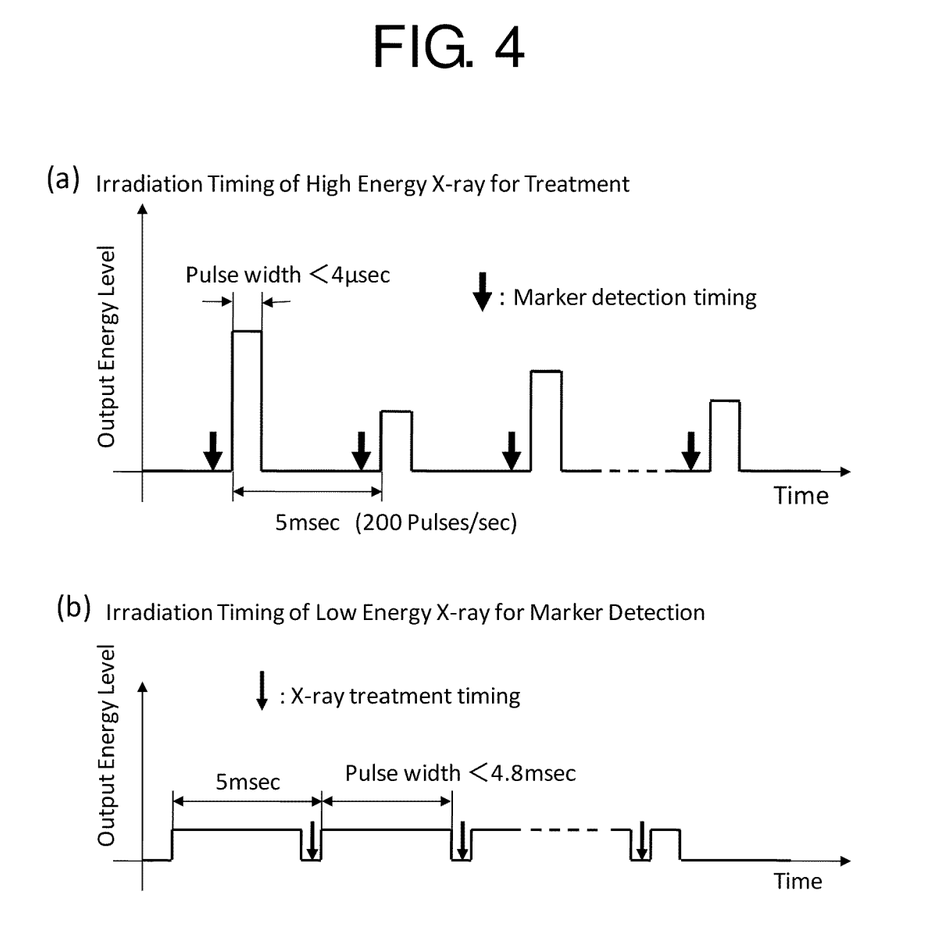
FIG. 4 shows wave form charts to explain the radiation motion of the X-ray source of the X-ray treatment apparatus in accordance with an embodiment of the present invention.

FIG. 4 (a) shows the radiation timing of the X-ray for treatment and FIG. 4 (b) shows the radiation timing of the X-ray for detecting marker. The X-ray for detecting marker is irradiated in the interval of the radiation by the X-ray for treatment, the next radiation of the X-ray for treatment is performed according to the detected data by the X-ray sensor for treatment and the X-ray sensor for detecting marker. The X-ray radiation for treatment continues 200 pulses per second for around 10 minutes. The energy level of the one shot of the X-ray for treatment is low level so as not to damage normal tissue. Because the X-ray for treatment of about 120,000 pulses concentrates on the tumor of the treatment object from particular directions which are decided in the treatment plan beforehand, the dosage is enough to damage the cancer cells.

The treatment using the X-ray treatment apparatus in accordance with an embodiment of the present invention is performed based on the original treatment plan which is decided by the doctor synthetically with the data obtained by the sensors of the X-ray treatment apparatus and the data obtained by other inspection apparatus such as calculated tomography. The original treatment plan includes the direction of the X-ray beam, the profile of the X-ray beam and the intensity of the X-ray beam in a series of radiation. The steps of the treatment are as follows. (1) The X-ray generators for detecting marker 3L, 3R are started, the tumor and the domain including the markers are irradiated with the low energy X-ray, and the position of the marker is detected, and the captured image data of the marker is compared with the data of the original treatment plan. (2) The X-ray generator 1 for treatment is started, and the high energy X-rays which have the profile of the beam and the intensity determined in the treatment plan irradiate the tumor. (3) The radiation of the X-ray generator 1 is detected by the X-ray sensor 10 for treatment at the same time. (4) The conditions such as the intensity and the profile of the X-ray beam for the next radiation are adjusted according to the results of the steps of (1) and (3). In the next radiation the steps of (1)-(3) are repeated. As mentioned above, the method for treatment using the X-ray treatment apparatus in accordance with an embodiment of the present invention can provide optimal treatment by adjusting in real time the profile and the dosage of the X-ray for treatment according to the image data obtained with the X-ray sensor 10 and the X-ray sensor 4L, 4R or the combinations of these image data.

The X-ray source for treatment used with the X-ray treatment apparatus in accordance with an embodiment of the present invention has been developed to fit a new technique called MMRT by the same inventor as the present invention, and it was already filed on Dec. 10, 2008 as title of the invention "X-ray generator" (U.S. patent application Ser. No. 12/332,100).

This X-ray source is explained in association with the treatment apparatus in accordance with an embodiment of the present invention as follows.

Figure 2A:
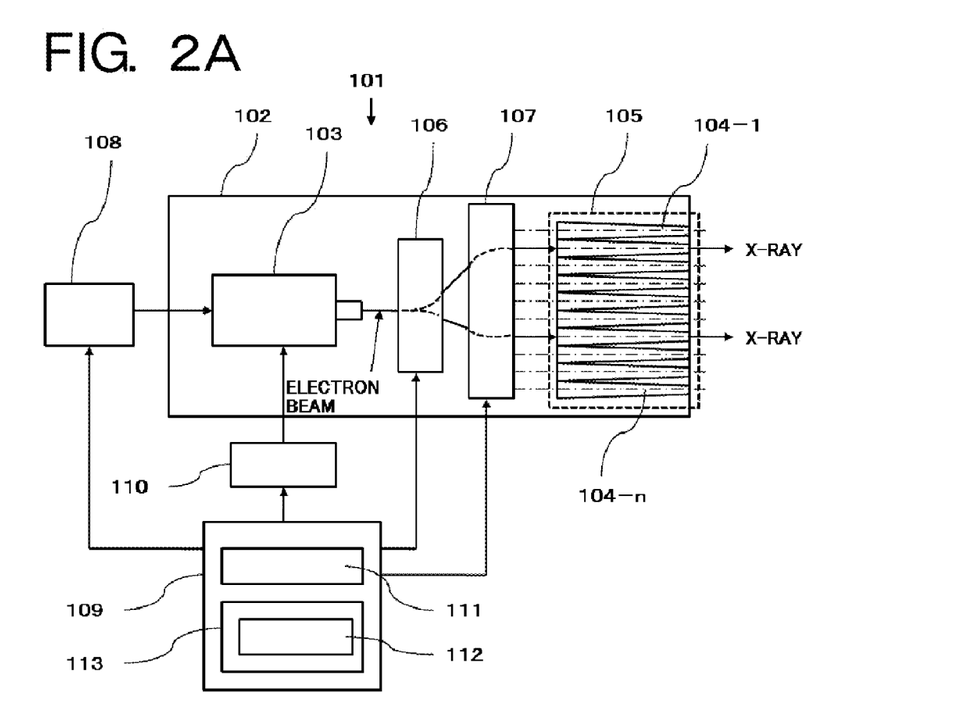
FIG. 2A shows a block diagram showing a first embodiment of the X-ray source to use with the X-ray treatment apparatus in accordance with an embodiment of the present invention.
Figure 2B:
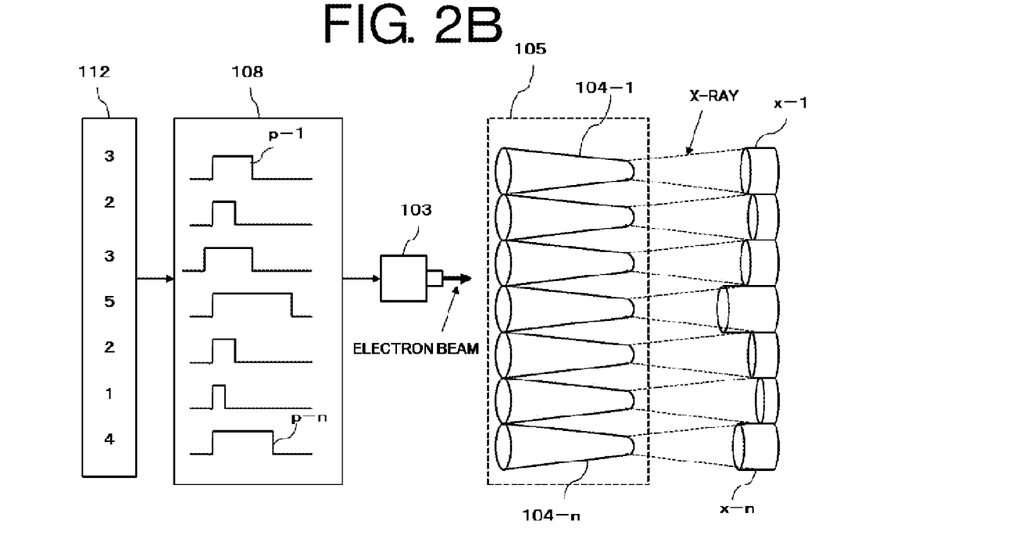
FIG. 2B shows an explanatory drawing showing the state to modulate the intensity of the radiation field of a first embodiment of the X-ray source to use with the X-ray treatment apparatus in accordance with an embodiment of the present invention.
Figure 2C:
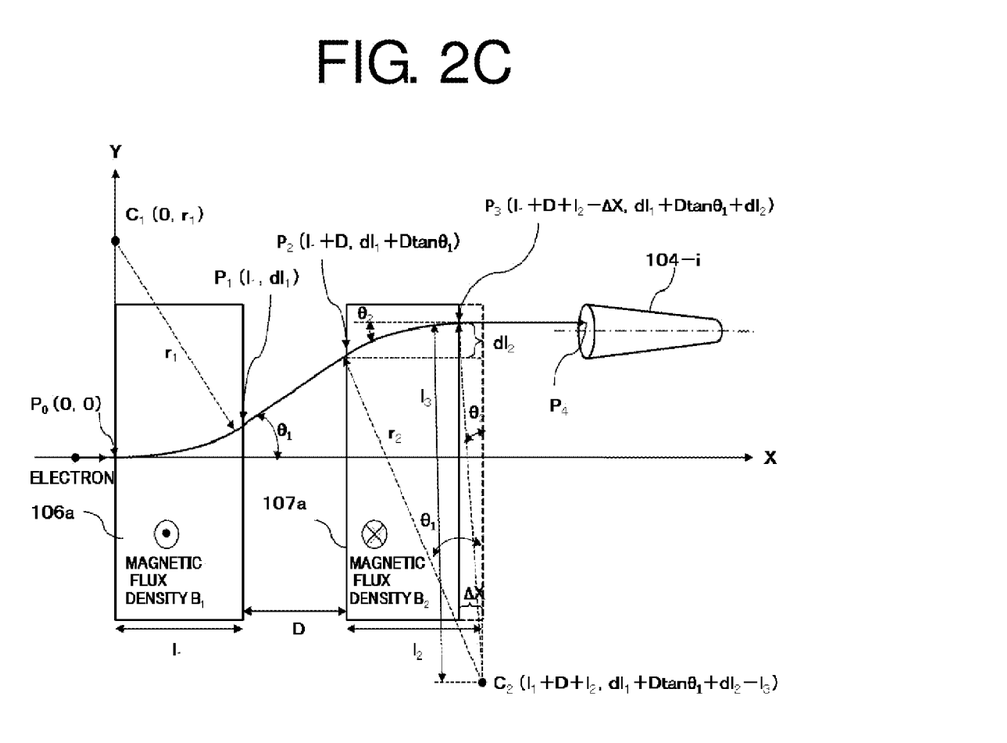
FIG. 2C shows an explanatory drawing showing the deflection of the electron beam of a first embodiment of the X-ray source to use with X-ray treatment apparatus in accordance with an embodiment of the present invention.

FIG. 2A is a block diagram showing a first embodiment of the X-ray source used with the X-ray treatment apparatus in accordance with an embodiment of the present invention, FIG. 2B is an explanatory drawing showing the operation of the X-ray source, and FIG. 2C is an explanatory drawing to explain the deflection of the electron beam in the X-ray source.

As shown in FIG. 2A, the X-ray generator 101 includes an electron source (hereinafter referred to as an electron gun) 103 irradiating high energy electron beams in a vacuum chamber 102, an X-ray target tube array 105 including a plurality of X-ray target tubes from 104-1 to 104-n which are arranged in line and radiate X-ray beams by collisions of the high energy electron beams, the first bending magnet 106 and the second bending magnet 107 deflecting the high energy electron beams. A power source 108 outputting the high energy pulse to the electron gun 103 with a predetermined timing, a microwave source 110 supplying the high voltage microwave to the electron gun 103 and a controller 109 controlling the power source 108, the microwave source 110, the first bending magnet 106 and the second bending magnet 107 are composed outside of the vacuum chamber 102. A radiation control program 111 and a radiation intensity data 113 of the treatment field included a radiation intensity data 112 of the radiation field of the X-ray target tube array 105 are stored in the controller 109. The radiation intensity data 112 of the radiation field presents a radiation dosage of each X-ray target tube from 104-1 to 104-n. The radiation control program 111 controls the high voltage microwave source 110, the excitation of the first bending magnet 106, the second bending magnet and the width of the high energy pulse outputting from the power source 108 so that the high energy electron beams are incident in turn on the X-ray target tube from 104-1 to 104-n arranging in line.

FIG. 2B shows the state of the modulated intensity for the radiation field of the X-ray target tube array 105 in accordance with the radiation intensity data 112 of the radiation field. As shown in FIG. 2B, when the high energy pulse from p-1 to p-n corresponding to the desired dosage is output from the power source 108, the electron beams corresponding to the high energy pulse from p-1 to p-n are radiated in turn from the electron gun 103. The X-ray beams from x-1 to x-n are radiated by the electron beams colliding with the inner wall of the X-ray target tube from 104-1 to 104-n. The intensity of the X-ray beam from x-1 to x-n is modulated corresponding to the radiation intensity data 112 of the radiation field. The first bending magnet 106 and the second bending magnet 107 shown in FIG. 2A are the electromagnet of the parallel planes respectively. The first bending magnet 106 acts to bend the high energy electron beams to the direction of the desired target tube in the X-ray target tube array 105. The second bending magnet 107 deflects the high energy electron beams so that the direction is in parallel to the medial axis of the desired X-ray target tube. FIG. 2C shows diagrammatically the state that the electron is deflected.

Figure 2D:
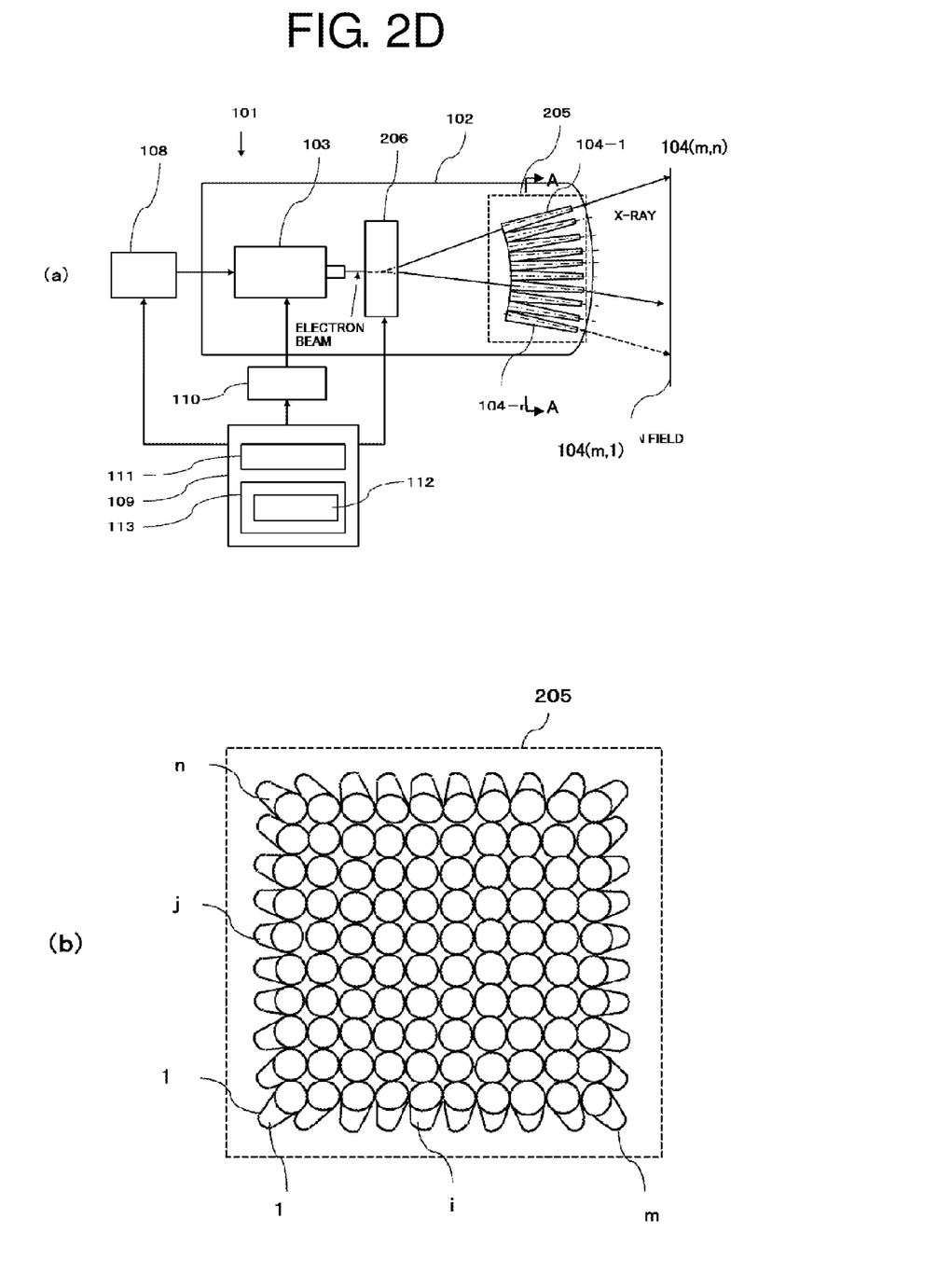
FIG. 2D shows a block diagram of a second embodiment of X-ray source to use with the X-ray treatment apparatus in accordance with an embodiment of the present invention (a) and a plan view showing an arrangement of target tube array, viewed arrows A-A in the block diagram (b).
Figure 2E:
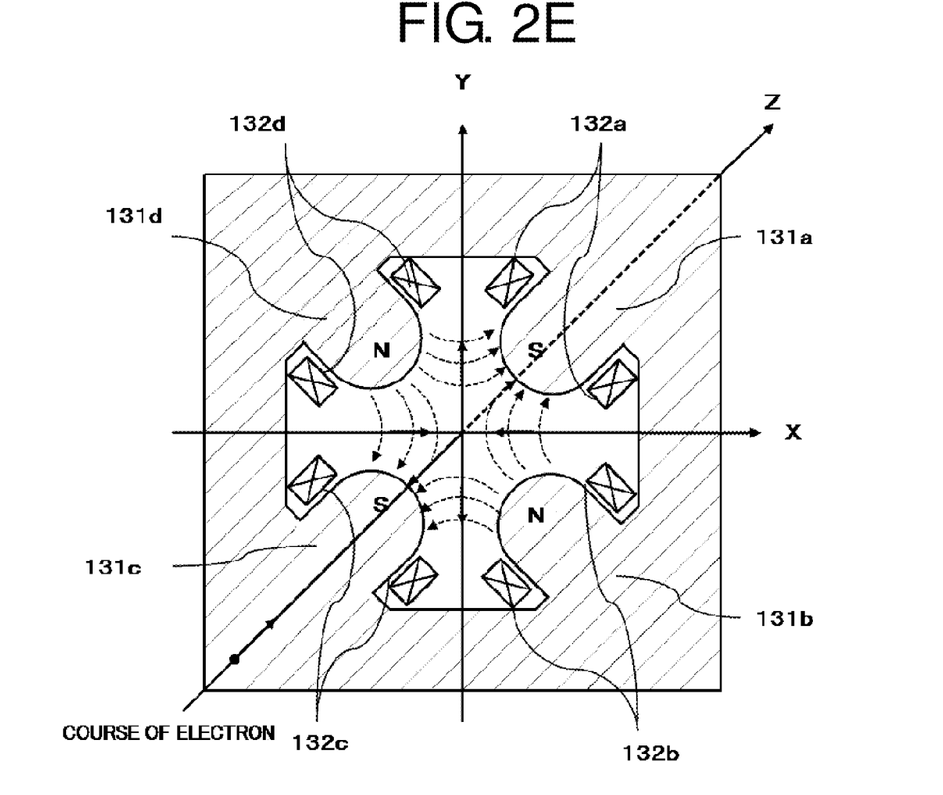
FIG. 2E shows a cross-section view of a bending magnet of a second embodiment of X-ray source of FIG. 2D.

FIG. 2D (a) shows a second embodiment of the X-ray source used with X-ray treatment apparatus of the present invention, FIG. 2D (b) is a sectional view of the X-ray target tube array 205 taken along the line A-A of FIG. 2D (a). FIG. 2E is a sectional view showing an embodiment of the quadrupole magnet 206. The common parts of the first embodiment and the second embodiment are shown with the same number. In the second embodiment, the X-ray target array 205 is composed of the target tubes which are arranged in matrix as shown FIG. 2D (b), and the high energy electron beam is irradiated to the X-ray target array 205 while scanning. In addition, the high energy electron beam deflected by the quadrupole magnet 206 can be incident on the inlet aperture of the X-ray target tube 104 ($i, j$) in parallel with the medial axis of each X-ray target tube 104 ($i, j$) by arranging radially the X-ray target tube 104 ($i, j$). According to this arrangement, for example, the radiation field of the X-ray target tube array 205 can be formed like 50 mm×50 mm radially in the position where is 50 cm away from the outlet apertures of the X-ray target tube array 205. The quadrupole magnet 206 which can deflect in two-dimensional direction is placed instead of a first bending magnet 106 and a second bending magnet 107 which deflect the travelling direction of the high energy electron in one-dimensional direction in the first embodiment. FIG. 2E is a cross section view of the quadrupole magnet taken cut along the perpendicular face (X-Y-axis plane) to travelling direction (Z-axis direction) of the electron beam. In FIG. 2E, the quadrupole magnet consists of the four magnetic cores 131a-131d and magnetizing coils 132a-132d wound up to each magnetic core. The magnetic fields generate in the direction shown with the dotted line arrow in FIG. 2E by spreading exciting current in the coil. The direction of the magnetic fields can be set the opposite direction by reversing the polarity of the exciting current. In FIG. 2E, when the high energy electron beams are incident on the Z-axis direction (from the front to the back of the space), Lorentz force works in the direction of the solid line arrow. Thus, by controlling the magnitude of the exciting current and the polarity, the course of electrons can be deflected in the arbitrary direction of the X-Y-axis plane. The electrons via the magnetic field of the quadrupole magnet go straight on, and reach the inlet aperture plane of the X-ray target tube array 205.

Figure 2F:
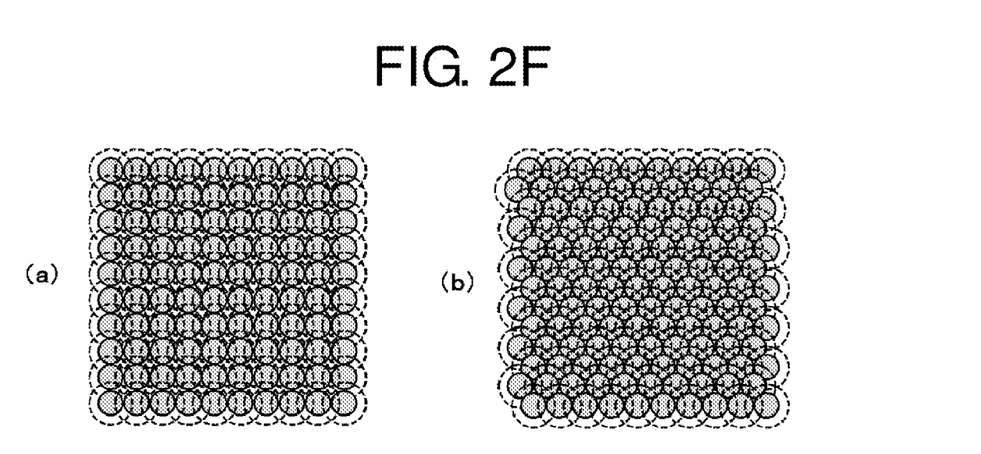
FIG. 2F shows diagrams describing the radiation field of a second embodiment of X-ray source of FIG. 2D.

The X-ray target tubes 104 ($i,j$) are arranged in a matrix shape as shown in FIG. 2D(b), even more particularly, the inlet aperture plane is placed radially so that the electrons deflected by the quadrupole magnet are horizontally incident on the inlet aperture for a medical axis of the X-ray target tube 104 ($i,j$). Thus, the X-rays are radiated radially from the X-ray target tube array 205, the radiation field is formed as shown FIG. 2F. The radiation field of the X-ray target tube array 205 is formed so that the radiation fields of ½ width are adjacent like the case of the first embodiment. In the second embodiment, because the radiation of the X-ray target tube 104 ($i,j$) is adjacent a matrix shape, the adjacent way such as the case which the ½ width of the radiation field adjoins with four places as shown in FIG. 2F(a) and with six places as shown in FIG. 2F(b) are considered. For example, in a case in which the radiation field of 50 mm×50 mm is formed at the position of 50 cm from the outlet aperture of the target tube array 205, the diameter of the ½ width in the X-ray target tube 104 is supposed to be 1 mm, when the configuration adjoining with four places of the adjacent X-ray target tube is adopted, the X-ray target tube array 105 is composed of 250 X-ray target tubes. The radiation intensity of each X-ray target tube 104 ($i,j$) is based on the radiation intensity data 112 such as the first embodiment. The order of the scan in irradiating is selectable according to the operating condition, such as the scanning from the center for the outside course of the radiation field, the scanning from the circumference to leave for the center and the scanning of the direction of row or column from one corner for the other corner. As explained above, according to the second embodiment, because the target tube array 205 is arranged radially, the radiation field can be formed widely.

Thus, because the X-ray treatment apparatus using the second embodiment of the X ray source can shorten the treatment time than the X-ray treatment apparatus using the first embodiment of the X ray source without moving the X-ray generator or the couch, the suitable X-ray treatment apparatus for MMRT can be provided.

Figure 3A:
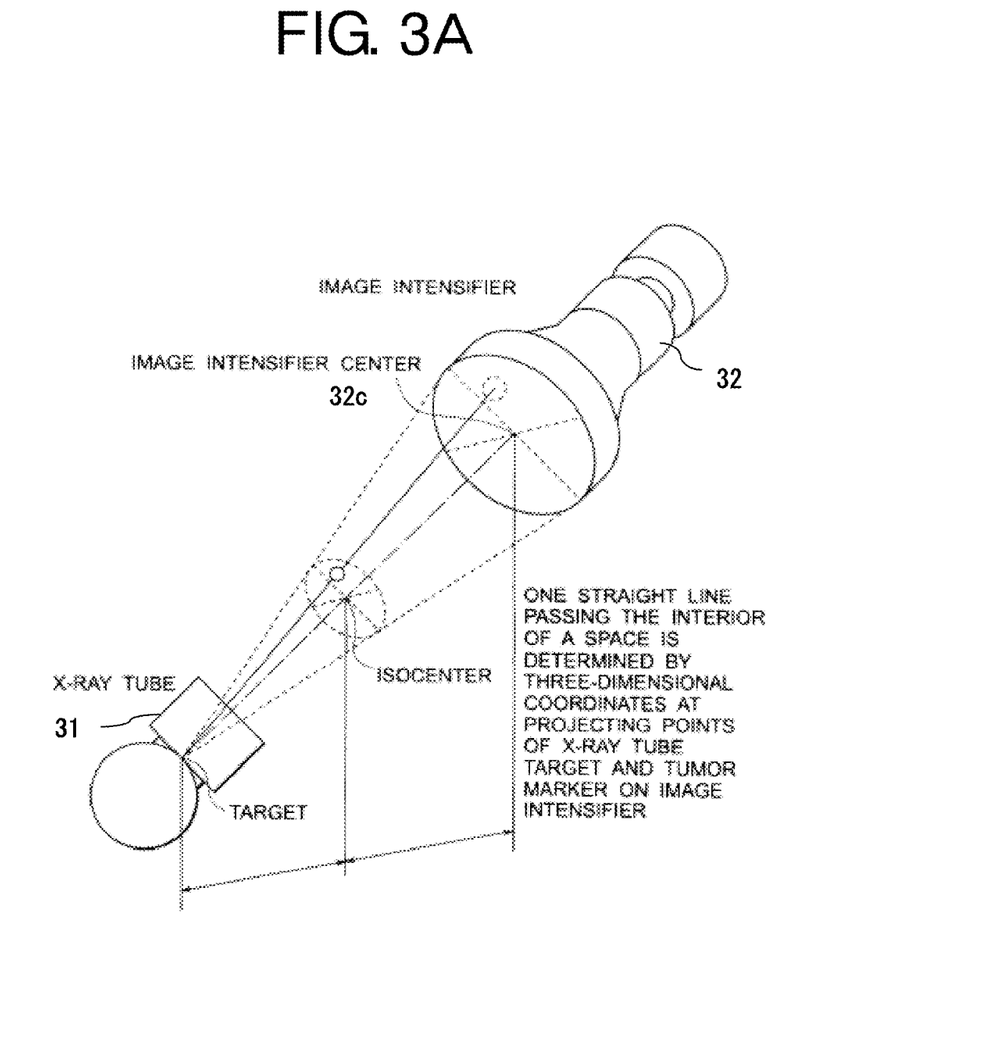
FIG. 3A shows a perspective diagram showing a pair of X-ray source and sensor used in a moving body tracking technique in a conventional embodiment.
Figure 3B:
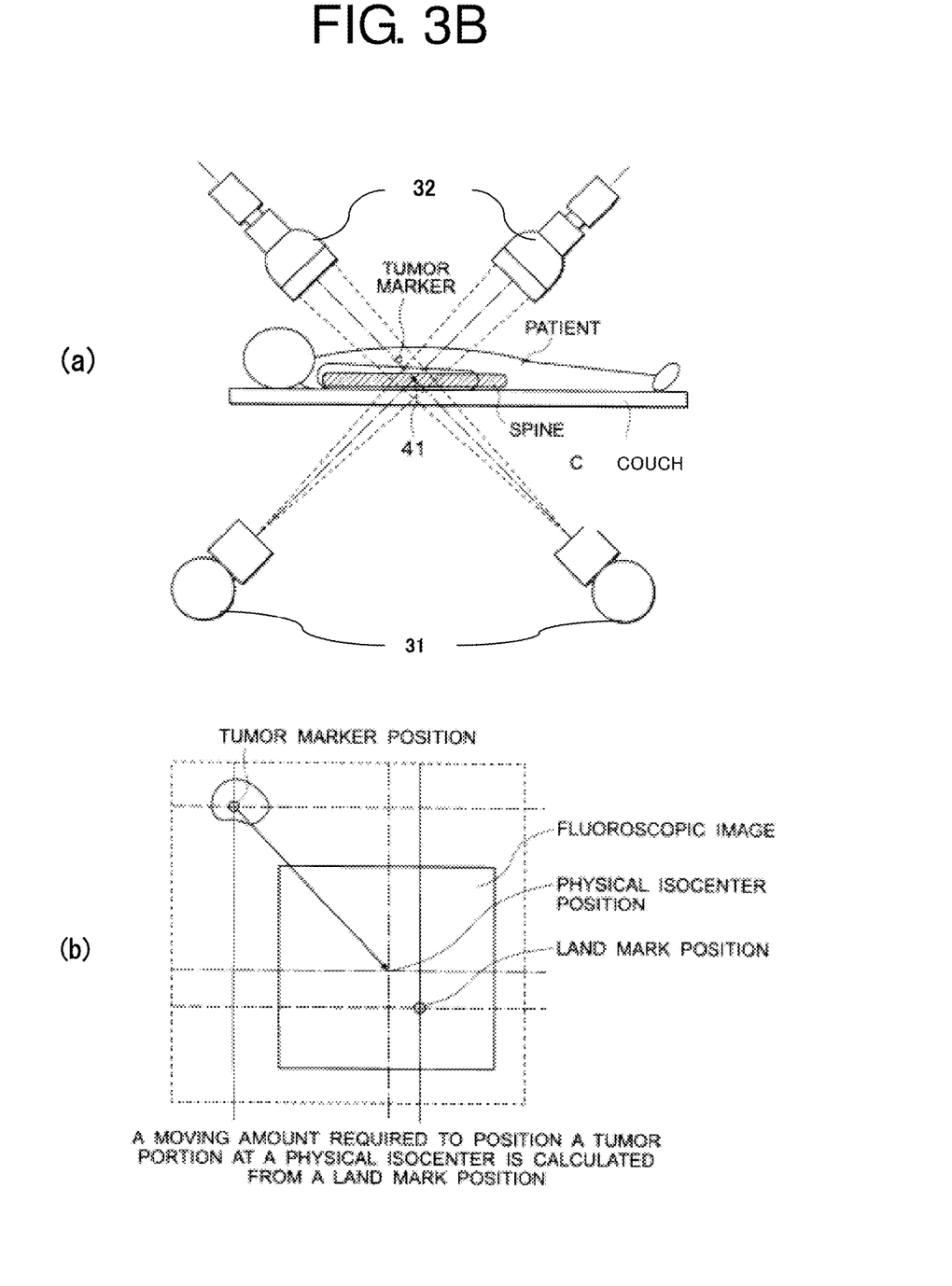
FIG. 3B shows a schematic drawing to explain the motion of a moving body tracking technique in a conventional embodiment.

The moving body tracking technique which tracks in real time the markers embedded in the body moving due to breathing and others is a well-known technique, as shown in U.S. Pat. No. 6,307,914 (hereinafter referred to as Hokkaido University method). In the present invention, the improved Hokkaido University method is utilized for detecting a marker relative to the couch 2. The Hokkaido University method uses the X-ray tube 31 as shown in FIG. 3A and a pair of image intensifier 32 as shown in FIG. 3B(a). By this, the position of a tumor marker to the referenced space and the physical isocenter 41 are acquired as shown in FIG. 3B(b). In the Hokkaido University method, tracking the marker, the X-ray for treatment can be irradiated only while the calculated three-dimensional coordinate of the marker exists within the predetermined range. Conventional moving body tracking techniques other than the Hokkaido University method involve measuring how far the moving body has moved from the isocenter (which is the reference point), and the X-ray for treatment is radiated after estimating the movement of the moving body according to the data of the measured movement. In contrast, in an embodiment of the X-ray treatment apparatus of the present invention, the X-ray for treatment irradiates the tumor according to the position information of the marker detected with the marker sensors 4L, 4R installed in the couch 2. At the same time, the irradiated X-ray for treatment is detected and information concerning the position of the irradiated X-ray and the direction by the X-ray sensor 10 is used to calculate the optimal radiation condition for the next radiation with the detected information and any modified position information of the marker. In an embodiment of the present invention, while tracking the movement of the marker, the X-rays for treatment can be radiated in succession. By this technique, the radiation accuracy and the radiation time are improved, as a result of which the treatment time can be shortened, and the burden on the patient can be reduced. The X-ray sensors and the couch can move together as a single integrated unit by applying the solid-state image sensor like a flat panel sensor instead of the image intensifier as the X-ray sensor. Even more particularly, radio waves can be used as another moving body tracking technique, in which case an IC Tag can be used as a radio wave transmitter. A plurality of IC Tags embedded in the vicinity of the tumor can be accurately recognized by the receiver incorporated in the positioning system in the IC Tag reader.

Various modifications and variations of the X-ray treatment apparatus of the present invention can be conceived within the scope of the present invention. The example of a six-axis or seven-axis robot arm was shown, but robots of other forms can also be utilized. The CT of a gantry or the circular rotational structure can be considered to a kind of the robot in a broad sense, and the X-ray source operative means should be interpreted broadly. An example in which the X-ray target tubes were drawn up in the X-ray generator for treatment was described, but, for example, the array of other shapes such as a spiral is also possible. Examples using a heavy metal that is harmless to the human body as a marker and the IC Tag system were described, but the use of other the active signal sources is also conceivable. An X-ray source was described as the source for treatment and detecting markers, but other sources can also be utilized. The X-ray treatment apparatus with the present invention is a medical instrument used for the treatment such as tumors in medical facilities such as hospitals.

What is claimed is:

1. An X-ray treatment apparatus irradiating to a lesion of a patient lying on a couch from different positions more than once, comprising:
    at least one movable marker sensor including a low energy X-ray generator and an image sensor corresponding to the low energy X-ray generator detecting a position relative to the couch of a marker fixed in the patient while maintaining a predetermined positional relationship of the marker to the lesion and obtaining data of the lesion;
    a couch operative means changing a position and a posture of the couch;
    a movable X-ray source for treatment controlling a beam profile and dosage of the X-ray for treatment by deflecting electron beams;
    movable X-ray sensor for treatment detecting the X-ray irradiated by the X-ray source for treatment, said X-ray having penetrated the lesion before being detected;
    an X-ray source for treatment operative means supporting the X-ray source for treatment, turned toward the lesion and controlling the position and posture of the X-ray source for treatment; and
    a central processing unit calculating a profile and dosage of the X-ray for treatment corresponding to a position of the lesion specified by outputs of the marker sensor based on a treatment plan, generating control signals to the X-ray source for treatment and the operative means, modifying the treatment plan according to output data of the X-ray sensor for treatment, and generating the next control signal to the X-ray source for treatment and the operative means.

2. The X-ray treatment apparatus of claim 1, wherein the X-ray source for treatment operative means comprises a head of a six-axis or seven-axis robot arm supporting the X-ray source for treatment.

3. The X-ray treatment apparatus of claim 1, wherein the X-ray source for treatment operative means comprises a gantry or a ring rotational structure supporting the X-ray source for treatment, collaborating with the movement of the couch, and determining the direction of the X-ray for treatment.

4. The X-ray treatment apparatus of claim 2, wherein the X-ray source for treatment comprises an X-ray tube array bundling a plurality of X-ray tubes generating a high energy X-ray more than 1 MV, and having a thin beam with a diameter in the range of from 1 mm to 10 mm.

5. The X-ray treatment apparatus of claim 4, wherein the activity of the X-ray target tubes is chosen according to the treatment plan.

6. The X-ray treatment apparatus of claim 2, wherein the marker sensor comprises two low energy X-ray generators and two image sensors corresponding to the low energy X-ray generators, turned toward the lesion, and outputting images of the lesion and the marker heavy metal that is harmless to a human body.

7. The X-ray treatment apparatus of claim 6, wherein the two low energy X-ray generators and the image sensors corresponding to the low energy X-ray generators are installed in a gantry.

8. An X-ray treatment method using the X-ray treatment apparatus of claim 2 irradiating based on a treatment plan in series multiple times, comprising the steps of:
    detecting a position of a marker by a marker sensor;
    irradiating to a lesion high energy X-rays for treatment;
    detecting the high energy X-ray for treatment that has penetrated the lesion by an X-ray sensor for treatment;
    modifying the data of the treatment plan according to the data of the X-ray sensor for treatment; and
    performing the next irradiation of the lesion.

9. The method of claim 8, wherein the X-ray treatment apparatus modifies the beam profile, the dosage and/or the radiation direction of the X ray for treatment according to the latest data of image data of the X-ray sensor for treatment and/or image data of marker sensor.

10. The X-ray treatment apparatus of claim 2, wherein the X-ray sensor for treatment detecting the high energy X-ray is installed under the couch.

11. The X-ray treatment apparatus of claim 3, wherein the X-ray source for treatment comprises an X-ray tube array bundling a plurality of X-ray tubes generating a high energy X-ray more than 1 MV, and having a thin beam with a diameter in the range of from 1 mm to 10 mm.

12. The X-ray treatment apparatus of claim 3, wherein the marker sensor comprises two low energy X-ray generators and two image sensors corresponding to the low energy X-ray generators, turned the direction of irradiation toward the lesion, and outputs the images of the lesion and the marker heavy metal that is harmless to a human body.

13. An X-ray treatment method using the X-ray treatment apparatus of claim 3 irradiating based on a treatment plan in series multiple times, comprising the steps of:
    detecting a position of a marker by a marker sensor;
    irradiating to a lesion high energy X-rays for treatment;
    detecting the penetrated high energy X-ray high energy X-ray for treatment that has penetrated the lesion by an X-ray sensor for treatment;
    modifying the data of the treatment plan according to the data of the X-ray sensor for treatment; and
    performing the next irradiation of the lesion.

14. The X-ray treatment apparatus of claim 3, wherein the X-ray sensor for treatment detecting the high energy X-ray is installed under the couch.

15. The X-ray treatment apparatus of claim 2, wherein the marker sensor comprises two low energy X-ray generators and two image sensors corresponding to the low energy X-ray generators, installed in a gantry, turned toward the lesion, and outputting images of the lesion and the heavy metal marker.

16. An X-ray treatment method using the X-ray treatment apparatus to irradiate a lesion of a patient lying on a couch from different positions multiple times in quick succession, the apparatus comprising:
    at least one movable marker sensor unit having a low energy X-ray generator and a corresponding image sensor for detecting a position relative to the couch of a marker fixed in the patient while maintaining a predetermined positional relationship of the marker to the lesion and obtaining data on the lesion;
    a first robot for changing a position and a posture of the couch;
    a movable X-ray generator for treatment controlling a beam profile and dosage of the X-ray for treatment by deflecting electron beams;
    a movable X-ray sensor for treatment detecting the X-rays irradiated by the X-ray generator for treatment after the X-rays have penetrated the lesion;
    a second robot supporting the X-ray source for treatment, turned toward the lesion, and controlling the position and posture of the X-ray generator for treatment; and
    a processor that calculates a profile and dosage of the X-ray for treatment corresponding to a position of the lesion specified by outputs of the marker sensor based on a preset treatment plan, generates a control signal that is transmitted to the X-ray generator for treatment and the operative means, modifies the treatment plan according to output data of the X-ray sensor for treatment in real time, and generates a next control signal to the X-ray generator for treatment and the second robot,
    the method comprising the steps of:
    detecting a position of the marker with the marker sensor;
    irradiating the lesion with high-energy X-rays for treatment from the X-ray generator for treatment;
    detecting the high-energy X-rays for treatment after the X-rays have penetrated the lesion with an X-ray sensor for treatment;
    modifying the beam profile, dosage, and/or radiation direction of the X-rays for treatment according to the latest data obtained by the X-ray sensor for treatment in real time using the processor; and
    performing a subsequent irradiation of the lesion.

17. The method according to claim 16, wherein the X-ray sensor for treatment forms a single integrated unit with the couch and is movable together with the couch by the first robot,
    the method further comprising the step of tracking movement of the X-ray generator for treatment with the X-ray sensor for treatment.

* * * * *